United States Patent [19]

Anapliotis et al.

[11] Patent Number: 5,184,602
[45] Date of Patent: Feb. 9, 1993

[54] ENDOSCOPE, IN PARTICULAR AN ARTHROSCOPE

[75] Inventors: Emmanuel Anapliotis, Berlin; Gisbert Schich, Ansbach, both of Fed. Rep. of Germany

[73] Assignee: Effner Biomet GmbH, Berlin, Fed. Rep. of Germany

[21] Appl. No.: 602,298
[22] PCT Filed: Nov. 19, 1989
[86] PCT No.: PCT/DE89/00728
  § 371 Date: Nov. 21, 1990
  § 102(e) Date: Nov. 21, 1990
[87] PCT Pub. No.: WO90/05479
  PCT Pub. Date: May 31, 1990

[30] Foreign Application Priority Data

Nov. 18, 1988 [DE] Fed. Rep. of Germany ... 8814573[U]
Mar. 29, 1989 [DE] Fed. Rep. of Germany ... 8904011[U]

[51] Int. Cl.⁵ .............................................. A61B 1/06
[52] U.S. Cl. .......................................... 128/6; 128/4
[58] Field of Search ...................................... 128/6, 4

[56] References Cited

U.S. PATENT DOCUMENTS

| | | | |
|---|---|---|---|
| 3,297,022 | 1/1967 | Wallace | |
| 4,153,356 | 5/1979 | Hama | 128/8 X |
| 4,319,563 | 3/1982 | Kubota | 128/6 |
| 4,705,023 | 11/1987 | Arai | 128/4 |
| 4,750,476 | 6/1988 | Forkner et al. | 128/6 |
| 4,756,304 | 7/1988 | Watanabe | |
| 4,819,620 | 4/1989 | Okutsu | 128/4 |
| 4,874,371 | 10/1989 | Comben et al. | 128/4 X |

FOREIGN PATENT DOCUMENTS

| | | |
|---|---|---|
| 1117256 | 11/1961 | Fed. Rep. of Germany |
| 2246182 | 3/1974 | Fed. Rep. of Germany |
| 7833379 | 2/1979 | Fed. Rep. of Germany |
| 3727190 | 2/1988 | Fed. Rep. of Germany |
| 8808299 | 8/1989 | Fed. Rep. of Germany |
| 1293091 | 4/1962 | France |

Primary Examiner—Richard J. Apley
Assistant Examiner—Karen Ann Richard
Attorney, Agent, or Firm—Spencer, Frank & Schneider

[57] ABSTRACT

An endoscope, in particular an arthroscope, includes an essentially cylindrical shaft containing optics and optical fibers, where the optical axis coincides with the longitudinal axis of the shaft and the optical fibers are arranged concentrically about the optics and a connecting piece preferably disposed radially to the longitudinal axis of the shaft via which the optical fibers are connected to a fiber-optic cable which leads to a light source. The direction of viewing at the end nearer the object is inclined to the longitudinal axis and at least the end of the optics nearer the object is arranged so as to rotate with respect to the connecting piece.

26 Claims, 7 Drawing Sheets

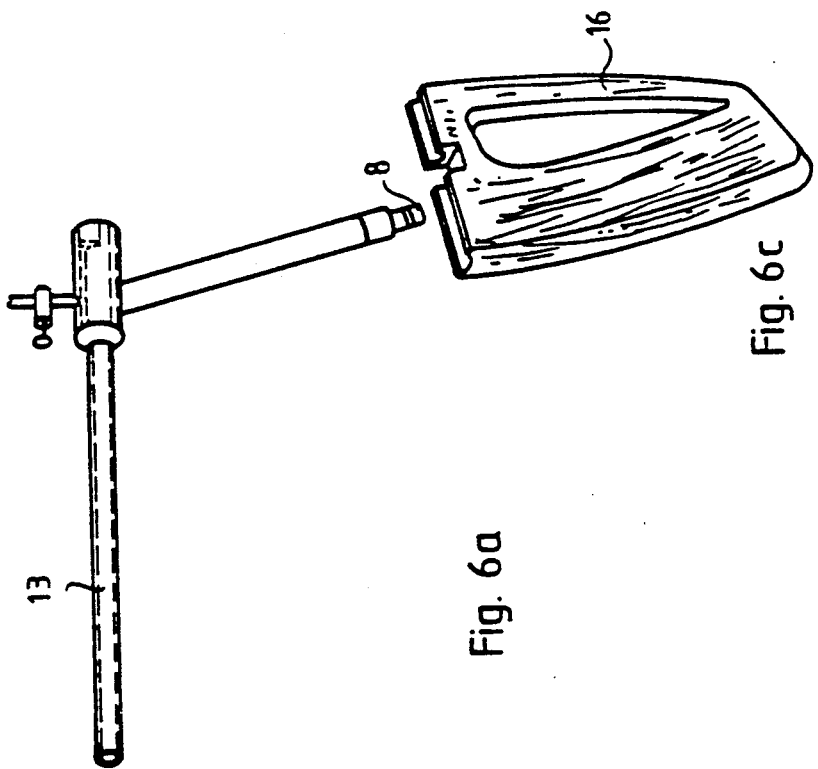

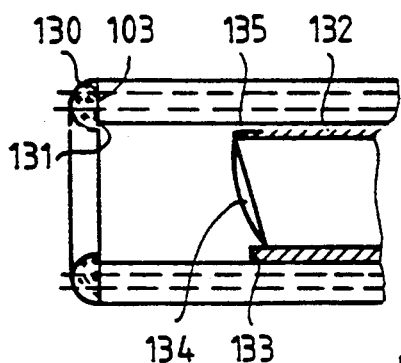
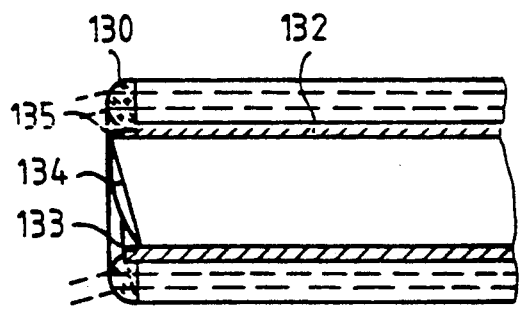
Fig. 11a  Fig. 11b
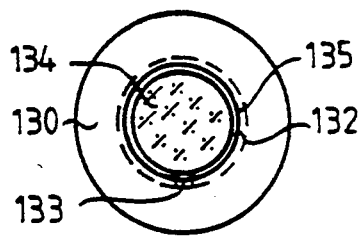
Fig. 11c
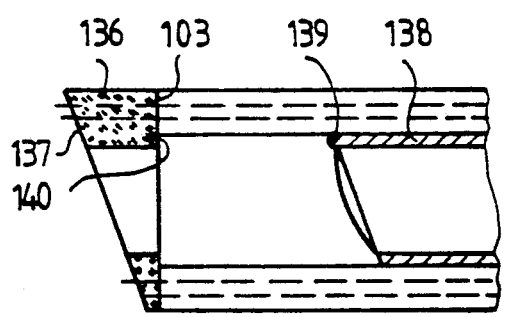
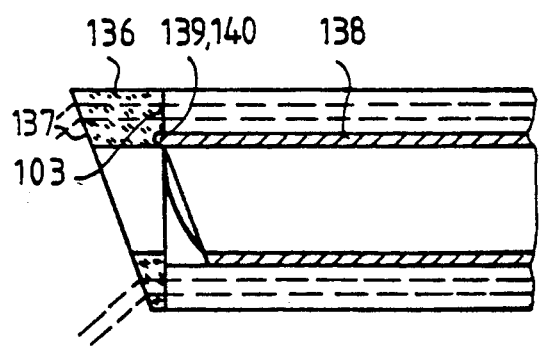
Fig. 12a  Fig. 12b
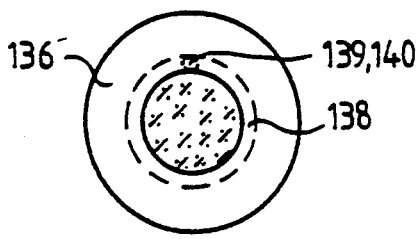
Fig. 12c

ENDOSCOPE, IN PARTICULAR AN ARTHROSCOPE

BACKGROUND OF THE INVENTION

1. Field of the Invention

The invention relates to an endoscope, in particular to an arthroscope having an essentially cylindrical shaft containing optics and optical fibers.

2. Background Information

Such endoscopes are used, in particular in the form of arthroscopes, to examine and treat acute articular joint spaces, and mainly those of the knee joint.

Endoscopes are known, that have an inclined direction of view relative to the optical axis in contrast to straight viewed optical means. The inclined viewing angle makes it possible to substantially widen the viewing area which is set by the direction of insertion by turning the instrument.

It is a disadvantageous fact that the connections, handles and picture analysis systems, in particular the connection piece for the light source, which usually projects radially out from the longitudinal axis of the instrument and the optical fiber cable leading to a light source must also be rotated when the whole instrument is rotated. Because of this the freedom of movement, in particular when implemented for medical use, is substantially impaired. Especially under surgical conditions every conduit which reduces the field of view or the work area acts as a considerable hinderance.

SUMMARY OF THE INVENTION

The object of this invention is to improve the ease of handling and at the same time to improve the implementation possibilities of the endoscopes known in the art and as described above.

This object is achieved by providing optics such that, at least at the end request the object to be viewed, the optics are arranged to rotate with respect to the connecting piece.

The invention is based on the realization that by rotating the optical part while the fiber optic light carrier is fixed in position an advantageous possibility exists, to alter the direction of view.

According to the invention, at least the end of the optical means nearer the object is rotatably connected relative to the connection. The rotation angle is preferably 360°.

The separate rotatability of the part of the shaft of the endoscope nearer the object enables an allround vision while avoiding that the cable connections, handles and picture analysis or recording devices situated on the ocular side are also undesirably rotated as well.

In accordance with an advantageous feature of the invention the sheath of the endoscope which contains optical means comprises two cylindrically shaped sections, whereby the division between the two sections is preferably situated between two optical elements and thereby allowing the part nearer the object to be rotatable about the longitudinal axis of the sheath.

The division is located behind the connection for the light source as viewed from the end nearer the object. The part of the endoscope nearer the object comprises the section of the sheath containing optical means nearer the object and a casing arranged concentrically around this section which holds the optical fibers, whereby the section of the sheath nearer the object is rotatable within the casing. The casing which holds the optical fibers is fixed in position relative to the section on the ocular side of the shaft of the endoscope. Only the region of the casing which is nearer the ocular can be rotated. In that way it is guaranteed, that for example picture analysis or picture recording instruments which are installed in the region of the endoscope shaft on the ocular side also are in a fixed position. The rotation of the region of the sheath containing optical means nearer the object also enables an "allround view" due to the sloping direction of view of the implemented optical means.

The rotatable part of the sheath containing optical means preferably stretches as far as a point close to the end facing the operator from where it is easy to handle the instrument. An operational element is preferably situated here which can be reached unproblematically from the outside when the optical fibers which surround the optical means have been previously branched off in a sideways direction. An "optical cutting point" is situated behind the operational element which enables the transistion to the fixed part of the remainder of the optical transmission path. Connected to this is the connection for a video camera which is also fixed in position.

A handle, which also contains the branched-off tubes for the optical fibers and connections for possible irrigation channels, mechanically "bridges" the region of the sheath containing optical means which can be accessed from outside and which is formed as the operational element. The multiple functions of such a handle are particularly advantageous. Besides being a comfortable support for the endoscope and the camera, the handle also serves as a guide for all of the tubes and leads in the direction of the endoscope. Obstruction of the operator due to freely hanging irrigation and/or suction tubes and optical fibers can thus be avoided.

In order that the object area is adequately illuminated, the angle of illumination of the optical fibers in the outlet area is adapted to correspond with that of the total possible observation area.

The end of the section nearer the object is formed by the light emission surfaces of the optical fibers and is shaped in the form of a truncated cone or in a concave fashion in the case of wide-angle illumination. This shape of the object side is in particular advantageous for arthroscopic examinations as it creates a gradual transistion between the light emission surfaces and the trepan which causes less injury to the cartilage during insertion into the articular joint space to be arthroscoped.

According to a special embodiment the optical fibers are divided at their ends nearer the object into an inner region which is directly adjacent to the sheath containing optical means with a light emission surface of a circular annular ring shape and into a peripheral outer region with a cone-shaped light emission surface. The division is preferably realized by the insertion of a ring with an essentially triangular cross-section.

In accordance with another feature all of the light emission surface is formed as a circular annulus and is covered with a frosted glass ring, which leads to a wide angled scattering of light. The glass ring preferably has a quarter circular cross-section, whereby the curved surface acts as a continual transistion from the side surface to the end face surface of the section nearer the object and therefore reduces the risk of injury.

The division between the sheath containing optical means can, for example, be formed as a dovetail joint or else as a screwed connection with a connection ring. In both cases both sections can be centered well and the rotatability is not limited in any way. In order to prevent an unintended turning of the threaded connection ring it can be stuck to or positively locked to a section of the shaft thereby fixing its position. The replacement or the addition of differing shaft sections is then no longer possible.

A knurled ring is used for easy handling of the rotatable part and is situated concentrically about the longitudinal axis at the end of the region nearer the object facing the connecting piece for the light source.

The rotation can also be carried out by a battery operated motor whereby the motor is connected to the section on the observation side in particular connected to or arranged in a handle and the motor shaft is in contact either directly or via gear elements with the periphery of the section nearer the object or with the periphery of the knurled ring and makes this carry out a rotational movement.

The division enables the section of the sheath containing optical means nearer the object to be rotated relative to the section of the sheath containing optical means further away from the object and it can also act as a connection for various sections nearer and further away from the object.

Other advantageous features of the endoscope according to the invention relate to variations for adapting the direction of illumination to the direction of view.

For this, preferably diversion prisms are inserted in the illumination sheath together with the tip of the sheath containing optical means and are folded out into the light path by a spring mechanism. When the sheath containing optical means is rotated inside the illumination sheath the prisms are also rotated so that the direction of illumination corresponds in every rotational position with the direction of view.

A further variation in order to influence the direction of illumination is based on the deformation of a transparent ring which covers one of the light-emission surfaces of the illumination sheath, which takes place when the sheath containing optical means is inserted and rotated and touches the protruding sections of the ring.

According to another variation a rotatably mounted cover of non-deformable, transparent material, in particular glass is provided on the light emission surface of the illumination sheath. The shape of the cover corresponds to that of a diversion prism with a centered bore through which the observation light path can pass. Due to this cover the light is diverted by a fixed angle. A sheath containing optical means with a direction of view corresponding to an inclined optical means can be connected to the cover so that the cover together with the sheath containing optical means can be rotated and the light can be diverted into the required direction of view.

BRIEF DESCRIPTION OF THE DRAWINGS

Further advantageous features of the invention will be described in greater detail below together with a description of the preferred embodiment of the invention as shown in the drawings, in which FIG. 6 is a perspective view of an endoscope according to FIG. 1, FIGS. 6a to 6e show individual parts of the endoscope according to FIG. 6.

FIGS. 11a, 11b, and 11c show a third variation of an embodiment as shown in the FIGS. 9a, 9b and 9c and FIGS. 12a, 12b and 12c show a fourth variation of an embodiment as shown FIGS. 9a, 9b and 9c.

DETAILED DESCRIPTION OF THE PREFERRED EMBODIMENTS

Figure 1:
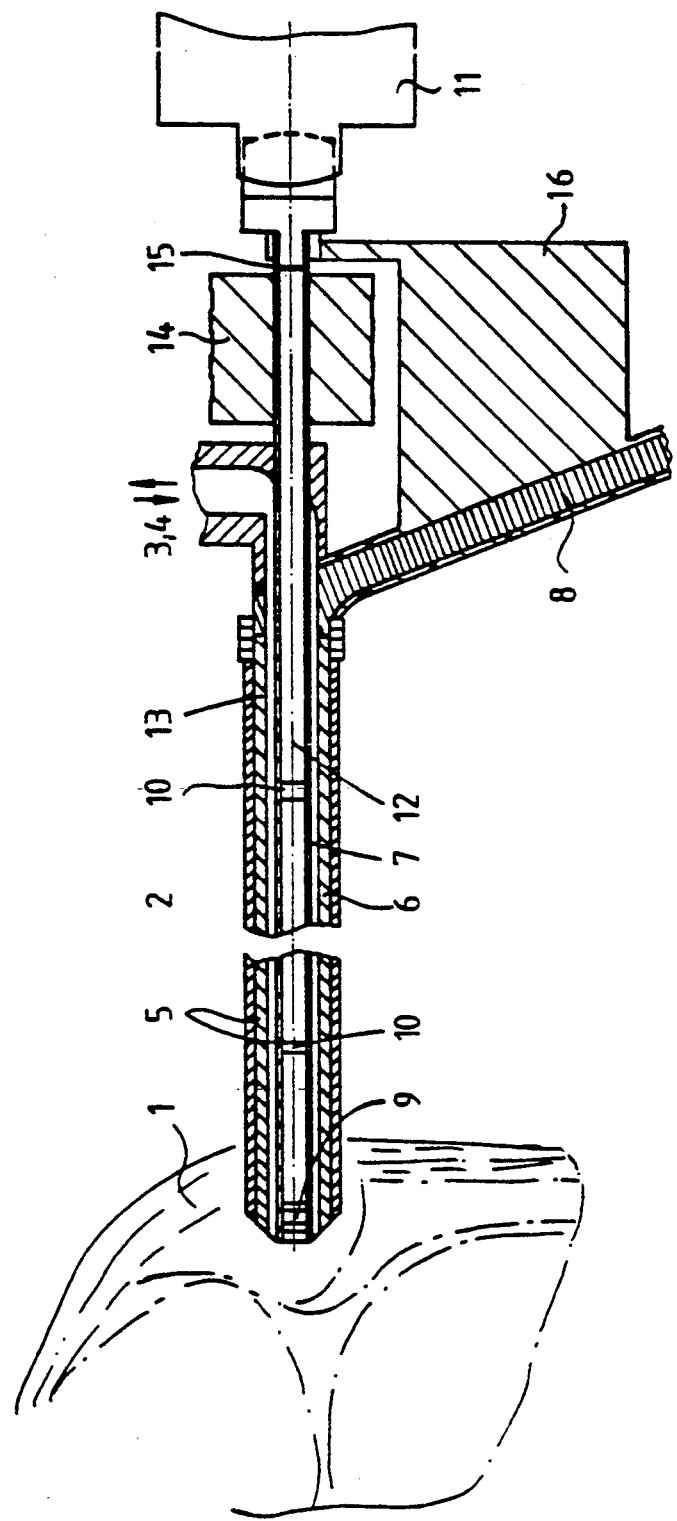
FIG. 1 is a longitudinal section through an arthroscope with a division.

A longitudinal section of an endoscope according to the invention in the embodiment as an athroscope to examine the joint space area of a knee joint is shown in FIG. 1. Such an athroscope comprises a trepan sheath 2, a suction- 3 and/or irrigation channel connection 4 and an endoscopic device 5, which can be inserted into the trepan sheath 2. The endoscopic device 5 comprises components for the illumination and the observation of the object. For this, optical fibers 6 which are arranged concentrically about the sheath containing optical means 7 are usually used for illumination and are connected to the light source via a sidewardly protruding light source connecting piece 8 and a fiber-optic cable. The suction and/or irrigation channel runs between the optical fibers 6 and the sheath containing optical means 7. Bars are provided, which are not shown in the drawing, for stabilization purposes and so as to act as spacers between the optical fibers 6 and the sheath containing optical means 7. The sheath containing optical means 7 comprises an objective 9 and a plurality of image displacement lenses 10 which either throw the object 1 onto the intermediate picture plane of an eyepiece for visual observation or project the image onto the endicon of a camera 11 for monitor observation or image recording. The optical axis 12 of the endoscope 5 coincides with that of the geometrical longitudinal axis of the trepan 2.

In the following description the "sheath containing optical means" only describes the rotatable section of the sheath containing optical means nearer the object.

The sheath containing optical means 7 can be rotated in a coaxial direction relative to a fixed camera 11 whereas the illumination part 13 comprising optical fibers is fixed in position.

A knurled ring 14, which can be accessed from the outside, is situated behind the illumination connecting piece 8, the knurled ring being connected to the sheath containing optical means 7. A division 15, behind the knurled ring 14, allows the sheath containing optical means 7 to be rotated relative to the camera part 11.

In this way it can be achieved, that the light connecting piece 8, the suction 3 and/or irrigation channel connection 4, the camera 11 and the handle or a holder 16 remain in a fixed position and do not also rotate if the sheath containing optical means is rotated.

Figure 2:
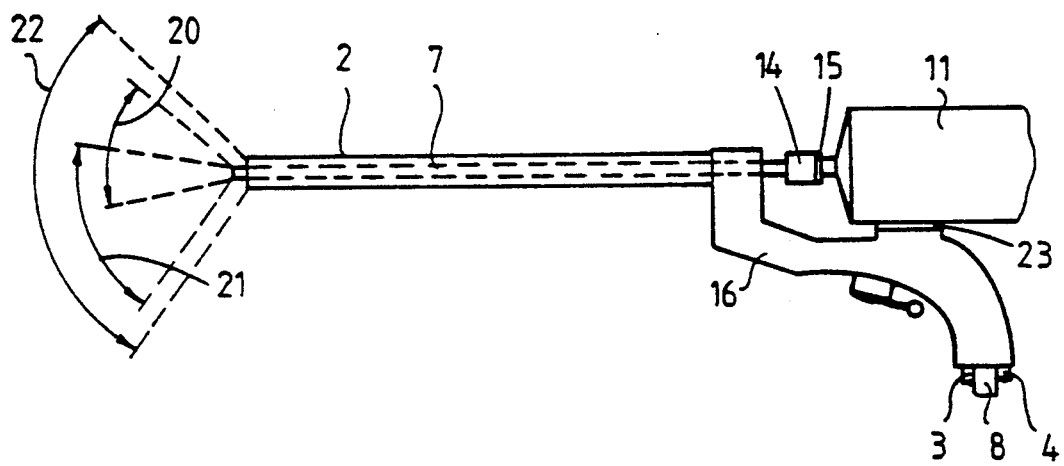
FIG. 2 shows another embodiment of the arthroscope according to FIG. 1.

FIG. 2 shows a further fundamental representation of the embodiment already described.

Figure 3:
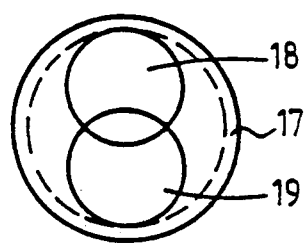
FIG. 3 shows the illuminated and the observed object area of the FIGS. 1 and 2.

In FIG. 2 and FIG. 3 the optical angle relationships of two positions of the shaft containing optical means 7 are illustrated which are rotated by 180° from each other. An area 17 (FIG. 3), which is substantially larger than the viewing area 18 or 19 (FIG. 3), is illuminated with an inclined direction of view to the optical axis 12. In a certain rotated position the angle area 20 and therefore the object area 18 are sighted and in a rotated position 180° from this position the angle area 21 and therefore the object area 19 are sighted. The illuminated room angle 22 or the illuminated area 17 remains constant. Advantageous embodiments of the light emission end on the side of the object for such a wide-angled illumination are illustrated in the FIGS. 5a and 5b.

The handle 16 as shown in the embodiment illustrated in FIG. 2 forms a bridge-like connection between the trepan sheath 2 and the fixed camera 11 and is also a holder for the connections and tubes which branch off before the knurled ring 14, in particular for the light connecting piece 8 and the suction or irrigation channel connection 3, 4. The camera 11 can be separated from the handle 16 at any time, due to the shoe connection 23, in order that the sheath containing optical means be withdrawn.

Figure 4:
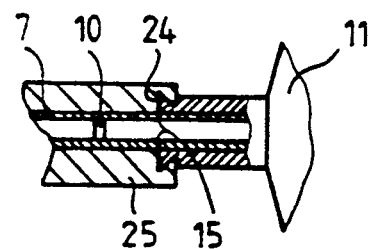
FIG. 4 shows a dovetail embodiment of a divide.

FIG. 4 shows a special variation of the division 15 in the form of a dovetail connection 24. This type of connection for cylindrical parts is characterized by being exactly centerable, simple in construction and by being of universal use. The part 25 of the dovetail connection 24 facing the end on the side of the object can also be used as a operating means for the rotational movement and is appropriately formed as a knurled ring for this purpose.

Figures 5A, 5B:
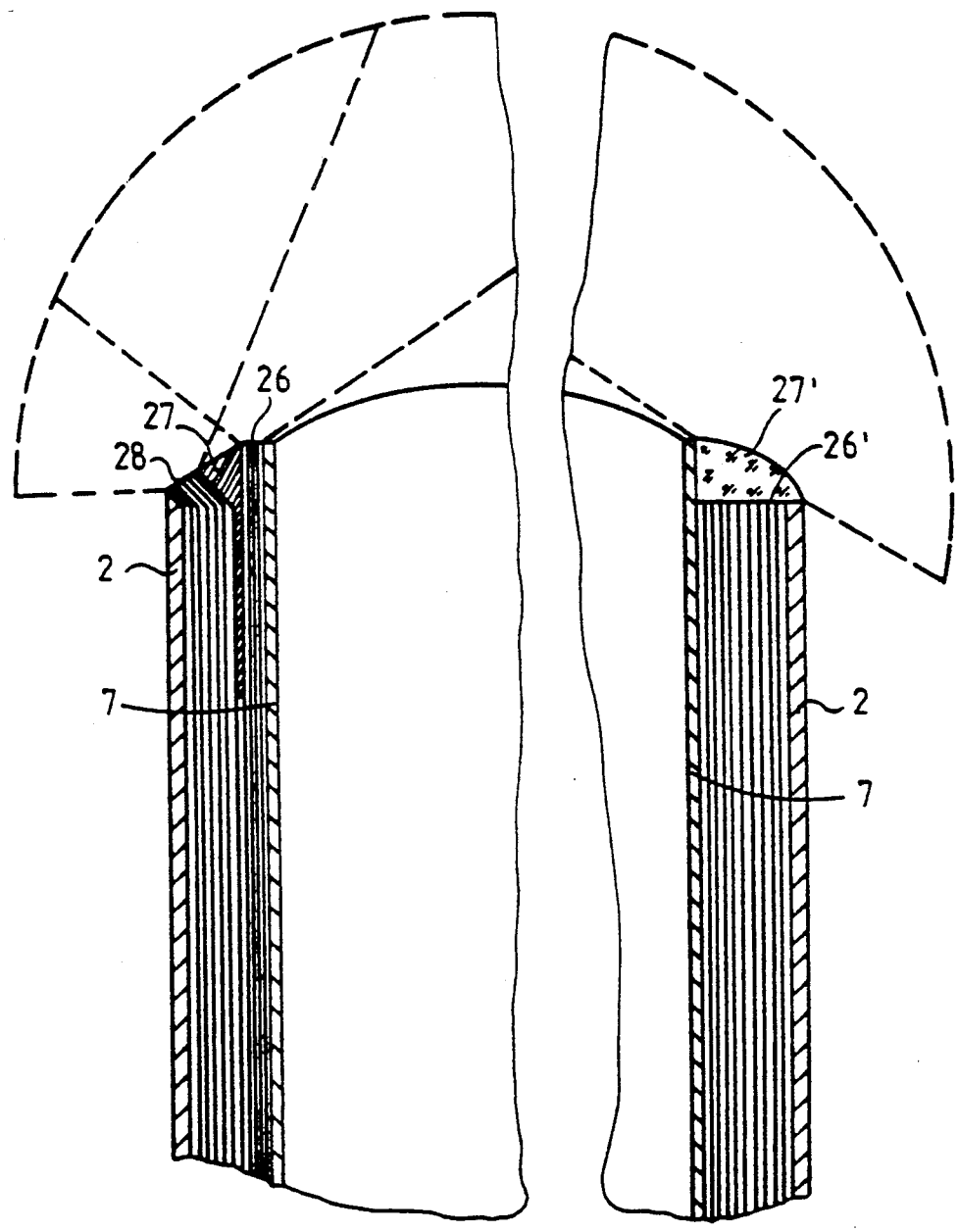
FIG. 5a shows a section through a side region of the end nearer the object of a first embodiment of a wide angle illumination.
FIG. 5b is a section though a side region of the end nearer the object of a second embodiment of a wide angle illumination.

FIG. 5a shows a first variation of a wide-angle illumination. This also comprises two annular light-emission surfaces which are separate from one another. An inner circular annular light-emission surface 26 which is directly adjacent to the sheath containing optical means 7 is separated from a conical light-emission surface 28 by a ring 27 with an essentially triangular cross-section. Both light-emission regions 26 and 28 and the ring 27 acting as a spacer form a smooth surface. This smooth surface is continued in the presence of the sheath of the trepan 2. Tissue damage during the insertion of the endoscope or athroscope can therefore largely be avoided. The angular regions of the light-emission areas overlap as shown in a dashed manner in FIG. 5a. It is also obvious, that in this way a very wide-angled illumination can be achieved.

With a second variation illustrated in FIG. 5b all of the light-emission surface 26' is shaped as a circular annulus. Instead of a spacer ring 27 a frosted glass ring 27' is provided, which lies in smooth contact with the light-emission surface 26' and whose cross-section is approximately quarter circular in shape. The frosting leads to wide-angled scattering of the light and due to the rounded-off cross-sectional shape of the glass ring 27' sharp edged corners which could lead to injury are avoided.

FIG. 6 shows a perspective view of an athroscope in accordance with the principle of the embodiment as illustrated in FIG. 1. The individual parts and the order of assembly are illustrated in FIGS. 6a through 6e. The endoscope comprises essentially an optical fiber illumination component 13 with a light connecting piece 8 (FIG. 6a), a rod-like sheath containing optical means 7 with a knurled ring 14 (FIG. 6b) with which to rotate the sheath containing optical means 7 about its optical axis 12, a connection 3 or/and 4 for a suction or/and irrigation channel which runs between the sheath containing optical means 7 and the illumination component 13, a handle 16 (FIG. 6c) and an adapter 29 (FIG. 6d) for a camera 11 (FIG. 6e). The light connecting piece 8 is advantageously integrated into the handle 16.

When the knurled ring 14 is worked the sheath containing optical means is rotated about its optical axis inside the suction/irrigation channel and the illumination component 13. The knurled ring 14 is situated directly adjacent to the handle 16 and can be easily accessed. The momentary direction of view can be ascertained from markings 30 on the knurled ring 14. The radial position of the markings on the knurled ring 14 coincide with the radial direction of view. It is also possible to project a mirror image of a marking, which shows the position of the knurled ring 14 and therefore the direction of view, into the optical image.

Figure 7:
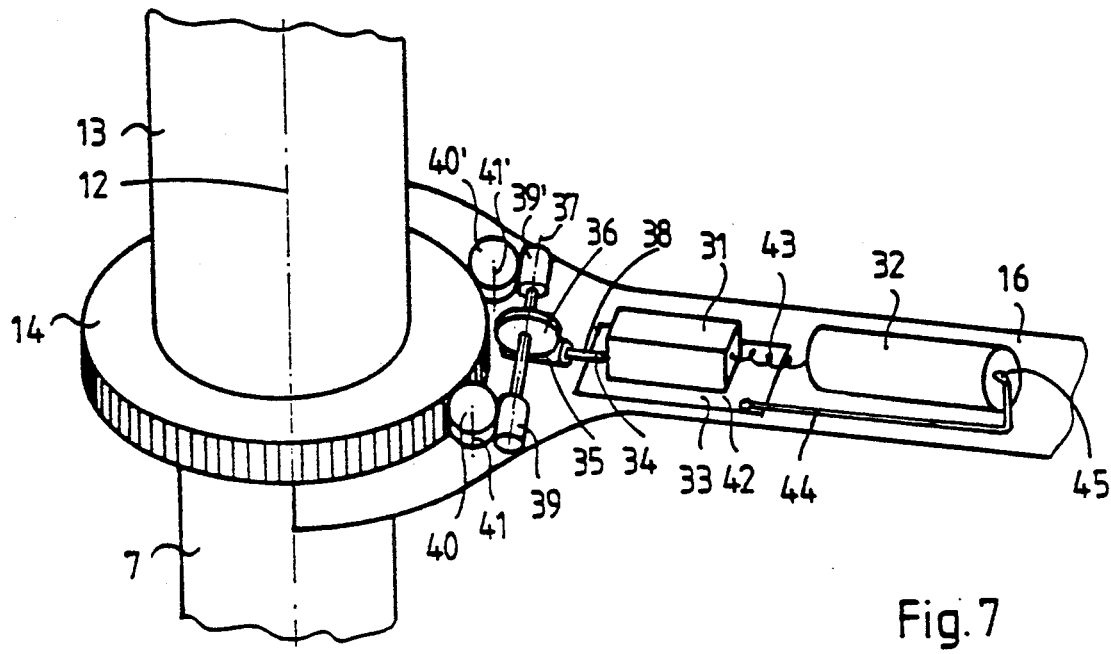
FIG. 7 shows a first variation of a motorized resetting of the knurled ring.
Figure 8:
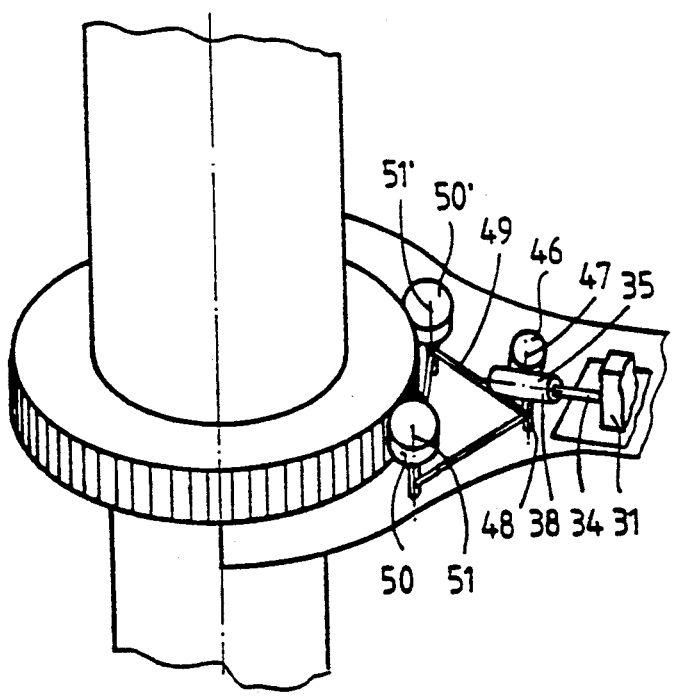
FIG. 8 shows a second variation of a motorized resetting of the knurled ring.

The variations of the motorized resetting means for the knurled ring 14 as illustrated in the FIGS. 7 and 8 comprise a motor 31 built into the handle 16 of the endoscope or the arthroscope, a battery 32 similarly built into the handle 16, a slide switch 33 and a number of gear elements, which transmit the energy of the motor 31 to the knurled ring 14 and thereby bring about a rotational movement of the sheath containing optical means 7 relative to the illumination component 13.

The gear elements comprise a worm gear/pinion combination in the first embodiment as shown in FIG. 7. The motor shaft 34 carries a worm gear 35, which is engaged with a pinion 36. The rotational axis 37 of the pinion 36 is directed in a radial plane of the knurled ring 14 and vertical to the rotational axis 38 of the worm gear 35. The pinion 36 is fixedly connected to two worm gears 39 and 39' via its axle. These worm gears 39 and 39' engage with two pinions 40 and 40' whose rotational axes are orientated in a direction vertical to the radial plane of the knurled ring 14 and vertical and symmetrical to the rotational axis of the worm gear 35. These pinioins 40 and 40' act as drive elements for the knurled ring 14. To be practical this type of knurling corresponds approximately to that of a rack.

A slide switch 33, situated in an ergonomically advantageous position on the handle 16 of the endoscope or athroscope, acts to turn the motor 31 on and off. Not only the electrical circuit is interrupted or closed but the transmission of force between the gear elements and the knurled ring is interrupted or created when the slide switch 33 is operated. This double function is advantageous because the manual rotatability of the knurled ring 14 is still possible. In order to be able to realize this double function the slide switch 33 is connected to a displacable foundation plate 42 on which the gear elements, the motor 31 and a flexible lead connection 43 and a connection lead 44 with a switch contact 45 situated between the motor 31 and the battery 32 are mounted. When the slide switch 33 is operated in the direction of the knurled ring 14 the foundation plate is also displaced, whereby the contact 45 is in contact with one pole of the battery and at the same time the gear elements are pressed onto the periphery of the knurled ring 14. The contact 43 between the displacable motor 31 on the foundation plate 42 and the battery 32 fixed to the housing of the handle 16 remains due to the flexibility of the contact 43 regardless of the switch position.

A further preferred embodiment, in particular with regard to the gear elements is illustrated in FIG. 8. The motor shaft 34 also carries a worm gear analogue to the embodiment shown in FIG. 7. A pinion 46 is engaged with it, whose rotational axis 47 is not only orientated in a direction vertical to the rotational axis of the worm gear 35 but is also orientated in a direction vertical to a radial plane of the knurled ring. A friction wheel 48 sits on the axis of the worm gear 46 and drives a belt 49, which in turn drives two rollers 50 and 50'. The rotational 51 and 51' axes of the two rollers 50 and 50' and the pinion 46 and therefore the friction wheel 48 are orientated in a direction vertical to the rotational axis 38 of the worm gear 35 and vertical to the plane of the knurled ring. The rollers 50 and 51' are, in addition, positioned mirror symmetrically to the plane of the rotational axes 38 and 47 in such a way that they are in contact with the periphery of the knurled ring 14. With the appropriate surface characteristics of the periphery of the knurled ring 14 and of the rollers 50 and 50' these move the knurled ring in a rotational direction by way of frictional contact.

Figure 9A:
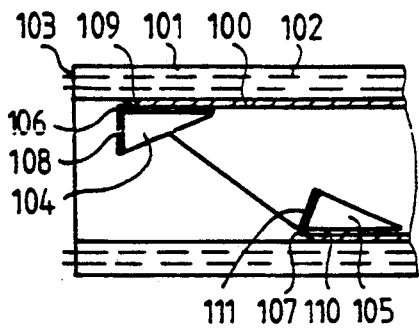
FIG. 9a shows a first variation of an embodiment of the distal end of the endoscope during the insertion phase of a sheath containing inclined optical means in partially sectional view.
Figure 9B:
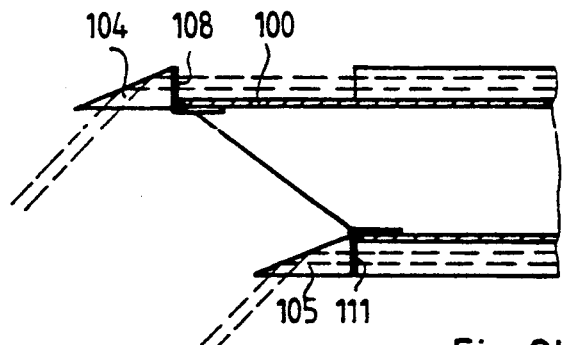
FIG. 9b is the view according to FIG. 9a after the sheath containing optical means has been inserted.

The FIGS. 9a and 9b show the end of an endoscope according to the invention on the side of the object during and after the insertion of a shaft containing optical means 100 with inclined optical means into a sheath-like illumination component 101 with straight illumination. The optical fibers 102, which act as the illumination, end at a light-emission area 103 shaped as a circular annular ring on the side of the object. In order to adapt the illumination component to the inclined optical means, the sheath containing optical means 100 to be inserted into the illumination sheath 101 comprises two angle prisms 104 and 105, whose diversion angles are adapted to the viewing angle of the inclined angle optical means. The prisms 104 and 105 are connected with oppositely disposed hinge joints 106 and 107 to the outer edge on the side of the object of the sheath containing the optical means 100. The corresponding edge areas of the sheath containing optical means 100 connected to the hinge joints 106 and 107 are assigned to the region of the angle objective which protrudes the most into the illumination sheath 101 and are also assigned to the region of the angle objective which is situated the furthest back. As soon as the sheath containing optical means 100 has been inserted into the illumination sheath so far, that a prism 104 projects out over the edge of the illumination, this prism 104 then folds outwards by 180°, whereby its surface area 108 is orientated in parallel to the light emission surface 103 of the optical fiber illumination means. The folding out is initated by a spring 109, which strives to take on the position as shown in FIG. 10b. A stop, whose effect is that the prism 104 does not fold out further than 180°, is built into the hinge joint 106. The hinge joint 107 does not comprise such a stop because the corresponding prism 105 folds out as far as the light emission surface 103 under the action of a spring 110 and therefore leads to the required light diversion. On the other hand, an air space exists between the other prism 104 and the light emission surface 103 when the optical shaft 100 is fully inserted.

When the sheath containing optical means 100 is withdrawn from the illumination sheath 101 both prisms 104 and 105 fold back in again and lie up against the corresponding inner wall of the sheath containing optical means 100 with an edge 112 or 113 which has been rounded off to correspond with the inner curvature of the sheath containing optical means 100. An angle objective, not shown in the FIGS. 9a and 9b, is positioned underneath the fold area of the prisms 104 and 105 inside the sheath containing optical means 100. The shadowing-off of the field of vision is not generally of great importance as the prisms become increasingly shorter with an increasing angle of the inclined optical means and therefore require less space for folding out.

Figure 9C:
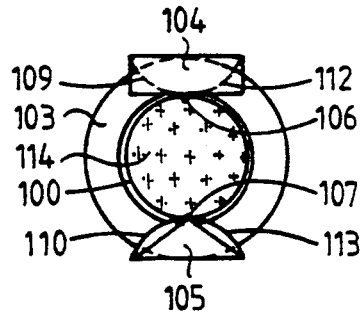
FIG. 9c is a face view of FIG. 9b

FIG. 9c shows a front view of the tip of the endoscope, whereby the light emission area 103, the prisms 104 and 105 in the folded out position, the end faces of the sheath containing optical means 100 and the angle objective can be seen.

Figure 9D:
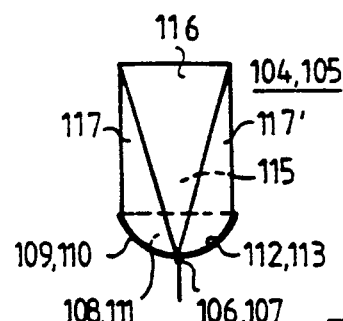
FIG. 9d shows a prism in perspective view as a detail of the FIGS. 9a, 9b or 9c.

The construction of both prisms 104 and 105 including the hinge joints 106 and 107 and the springs 109 and 110 is shown again in a perspective view in FIG. 9d. The prism 104 or 105 is limited by a base surface 108 or 111, a reflection surface 115, a light emission surface 116 and two rounded off side areas 117 and 117'. The side areas 117 and 117' form right-angled triangles in the projection.

Figure 10A:
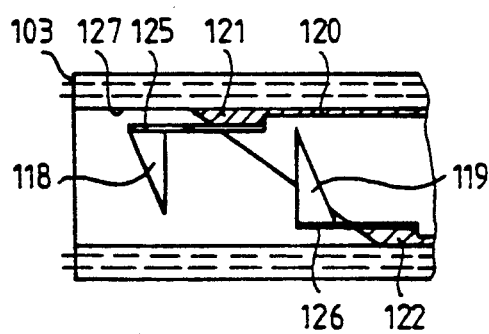
FIGS. 10a, 10b, 10c and 10d show a second variation of an embodiment as shown in the FIGS. 9a, 9b, 9c and 9d.
Figure 10B:
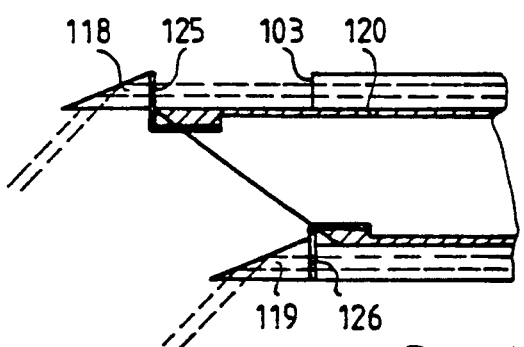

A second variaton of a sheath containing optical means comprising prisms 118 and 119 is shown in the FIGS. 10a, 10b, 10c and 10d and is illustrated in the same manner as in the FIGS. 9a, 9b, 9c and 9d. The prisms 118 and 119 are only folded out by 90° unlike the first variation. The sheath containing optical means 120 comprises two inwardly directed oppositely disposed attachments 121 and 122 on the side of the object. Due to the attachments 121 and 122, the tubular shaped sheath containing optical means comprises two level regions onto which the prisms 118 and 119 are connected by way of two hinge joints 123, 123' and 124, 124' respectively. During the insertion of the sheath containing optical means 120 the rectangular base surfaces 125 and 126 of the prisms 118 and 119—as shown in FIG. 10a—are pushed along the tubular inner wall 127 of the illumination sheath directly above the attachments 121 and 122. During the insertion only the side edges 128, 128' and 129, 129' of the base surfaces 125 and 126 touch this inner wall 127. In the inserted position, as shown in FIG. 10b, the prisms 118 and 119 are folded out by 90° into the illumination ray path.

Figure 10C:
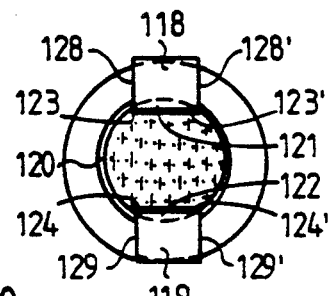

A front view is shown in FIG. 10c with both of the folded out prisms 118 and 119, the light-emission surface, the sheath containing optical means 120 and the angle objective.

Figure 10D:
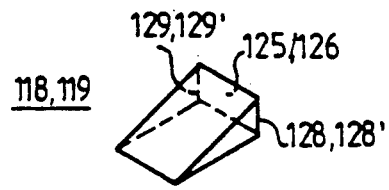

FIG. 10d shows a perspective view of the prisms 118 or 119. This prism 118 or 119 is of a simpler construction than the prism 104 or 105 of the first variation as shown in FIG. 9d due to the rectangular shape of the base surface 125 or 126.

In the third variation of the embodiment of a tip of an endoscope as illustrated in the FIGS. 11a, 11b and 11c, all of the light-emission surface 103 is covered with a ring 130 of flexible, transparent material whereby the cross-section of the ring 130 is essentially semi-circular. The ring 130 comprises a region 131 which protrudes out over the inner limit of the light emission surface 103 by a small amount. This region 131 is struck when the sheath containing optical means 132 is inserted and leads to the ring 130 being deformed in such a manner that the direction of illumination essentially corresponds to the direction of view of the inclined angle optical means. To this purpose the sheath containing optical means 132 comprises a protrusion 133 orientated distally and which is situated at the lowest point of the angle objective 134. The end of the sheath containing optical means 132 on the side of the object comprises a reduced wall thickness 135 over the remainder of the circumference, so that the protruding region 131 of the ring 130 can only be struck by the protrusion 133. If the sheath containing optical means 132 is rotated inside the illumination sheath in order to obtain an "allround view", the protrusion 133 connected to the sheath containing the optical means 132 touches the ring 130 in a circular path and which leads to different parts of the ring 130 being greatly deformed in turn elastically. Stays can be inserted between the sheath containing optical means and the illumination sheath in order to prevent the sheath containing optical means 132 from springing back onto the flexible ring 130.

The light emission surface 103 of the embodiment as shown in the FIGS. 12a, 12b and 12c is also covered with an annular cover 136 of transparent material which protrudes inwardly and slightly out over it. However, in contrast to the ring 130, this cover 136 is not elastic. The cover 136 lies in contact with and is rotatably mounted on the light-emission surface 103 of the optical fiber illumination means. The light-emission surface 137, situated opposite the contact surface of the cover 136, is inclined with respect to the contact surface or the light-emission surface 103 of the optical fiber illumination means, so that the light is diverted in one direction. In order that the direction of diversion of the light coincides with the direction of view of the optical means, a simple lock mechanism is provided for the sheath containing the optical means 138 and for the cover. For this, the distalmost end face area of the sheath containing optical means 138 comprises a locking pin 139 which engages in a corresponding slot 140 in the region of the contact surface of the cover 136 which protrudes inwardly, whereby the slot 140 is situated in the region of the cover which protrudes the most in the distal direction. When the sheath containing optical means 138 is rotated the cover is also rotated which leads to the direction of view of the inclined angle optical means and the direction of illumination corresponding with each other in every rotated position.

The present invention is not limited in its embodiment to the above-described preferred embodiment. Rather, a number of variations are conceivable which take advantage of the described solution even for basically different configurations.

We claim:
1. An endoscope, in particular an arthroscope, having an open front end, comprising:
an essentially cylindrical shaft containing an optical means for conveying optical images and optical fibers, an optical axis of the optical means coinciding with a longitudinal axis of the shaft, the optical fibers being arranged concentrically about the optical means;
wherein the optical fibers include a connecting piece disposed radially relative to the longitudinal axis of the shaft and by which the optical fibers are connected to a fiber-optic cable which leads to a light source, a direction of viewing at an end nearer an object being viewed is inclined to the longitudinal axis, and
wherein at least an end of the optical means nearer the object is arranged to rotate with respect to the connecting piece, the connecting piece not rotating when the optical means is rotated.

2. An endoscope according to claim 1, wherein a rotational angle of the optical means is essentially 360°.

3. An endoscope according to claim 1, wherein at least one region nearer the object comprising at least a portion of the total length of the optical fibers surrounding the optical means, is arranged in a fixed position with respect to the connecting piece.

4. An endoscope according to claim 1, wherein a divider is arranged behind the connecting piece as viewed from an end nearer the object.

5. An endoscope according to claim 4, wherein the divider is provided with a ring dovetail.

6. An endoscope according to claim 4, wherein the divider is provided with a screw connection comprising a connection ring.

7. An endoscope according to claim 6, wherein fixing means are provided for fixing a screwed position of the connection ring.

8. An endoscope according to claim 4, wherein the optical means is disposed in a rotatable sheath and wherein a knurled ring is arranged concentrically about the longitudinal axis of the rotatable sheath containing the optical means in a region adjacent to the divider.

9. An endoscope according to claim 4, wherein a battery-operated motor is provided, the motor having a shaft which engages one of directly and indirectly by gear elements with a periphery of the optical means and sets it in rotational motion.

10. A device according to claim 1, further comprising a handle which holds the connecting piece and is capable of accommodating at least one of suction and irrigation channels.

11. An endoscope according to claim 1, wherein an aperture angle of an illumination cone is greater than an aperture angle of an illumination ray path on a side of the object.

12. An endoscope according to claim 1, wherein the optical fibers are arranged such that an aperture angle of an illumination cone is at least 110°.

13. An endoscope according to claim 1, wherein a light emission surface of the optical fibers on a side of the object comprises an essentially conical or concave form.

14. An endoscope according to claim 1, wherein the optical means is disposed in a sheath and wherein the optical fibers form an inner region, directly adjacent to the sheath containing the optical means, having a light-emission surface in the shape of a circular annulus and form a peripheral outer region having a conical light emission surface at ends of the optical fibers nearer the object, and wherein a ring with an essentially triangular cross-section is provided to separate the two regions from one another.

15. An endoscope according to claim 1, wherein a ring of frosted glass is provided to cover a light-emission surface of the optical fibers in the shape of a circular annulus.

16. An endoscope according to claim 15, wherein the ring comprises a quarter circular cross-section, whereby a curved surface thereof forms an outer surface of an end of the endoscope on the side of the object.

17. An endoscope according to claim 1, wherein the optical means are disposed in a sheath and wherein the optical fibers form an illumination sheath, an end of the sheath containing the optical means nearer the object being provided with at least one diversion prism which can be folded out about an edge thereof and which is folded inside the sheath containing the optical means during insertion and withdrawal of the sheath containing the optical means from the illumination sheath, the at least one prism having at least one spring and folding outwards in the sheath inserted position with the help of the at least one spring so that a light entrance surface of the at least one prism is aligned in parallel with a light emission surface of the illumination shealth, whereby a direction of diversion and a diversion angle of a direction of view coincide with a viewing angle of the optical means.

18. An endoscope according to claim 17, wherein the at least one diversion prism can be folded out by 180° and comprises a curved edge between the light entrance surface and a curved light-emission surface thereof, the edge being provided with a hinge joint and the curvature of one of the edge and of the light-emission surface corresponds to an inner curvature of the sheath containing the optical means.

19. An endoscope according to claim 17, wherein the at least one diversion prism can be folded out by 90° and comprises a straight edge between a light entrance surface thereof and a light-emission surface thereof, wherein the edge is provided with at least one hinge joint embedded in the sheath containing the optical means.

20. An endoscope according to claim 1, wherein the optical fibers comprise an illumination sheath having a light-emission surface provided with a ring of flexible transparent material of a semi-circular cross-section having a region which protrudes inwardly over the light-emission surface, and wherein the sheath containing the optical means comprises a protrusion which deforms the protruding region of the ring by contact therewith so that illuminating light is diverted to correspond with a direction of view and a viewing angle of the optical means.

21. An endoscope according to claim 1, wherein the optical means is disposed in a sheath and the optical fibers comprises an illumination sheath, and wherein a cover of non-deformable transparent material is rotatably mounted on a circular and annular light-emission surface of the illumination sheath, a light-emission surface of the material being inclined with respect to the light emission surface of the illumination sheath, and wherein the sheath containing the optical means can be fixed to the cover so that illuminating light is diverted to correspond with a direction of view and a viewing angle of the optical means.

22. An endoscope, in particular an arthroscope, comprising:
an essentially cylindrical shaft;
optical means, disposed in said shaft and having an optical axis which coincides with a longitudinal axis of the shaft, for passing optical images of an area to be observed from one end of the endoscope to another; and
optical fibers disposed in said shaft for illuminating the area to be observed, the optical fibers being arranged concentrically about the optical means and having a connecting piece disposed radially to the longitudinal axis of the shaft by which the optical fibers are connected to a fiber-optic cable which leads to an external light source;
wherein a viewing direction at an end of the endoscope nearer to the area to be observed is inclined to the longitudinal axis of the shaft;
wherein at least the end of the optical means nearer the area to be observed is arranged so as to rotate with respect to the connecting piece;
wherein the optical means is contained in an inner sheath and said optical fibers form an illumination sheath arranged concentrically about the inner sheath; and
wherein an end of the inner sheath nearer the area to be observed is provided with at least one diversion prism which can be folded out about an edge, the at least one prism being folded inside the inner sheath during insertion and withdrawal of the inner sheath from the illumination sheath, the at least one prism having spring means for folding the at least one prism outwards after insertion of the inner sheath in such a manner that a light entrance surface of the at least one prism is aligned in parallel with a light emitting surface of the illuminating sheath, so that a direction of diversion of illumination coincides with a viewing angle of the optical means.

23. An endoscope according to claim 22, wherein the at least one diversion prism can be folded out by 180° and comprises a curved edge between the light entrance surface and a curved light-emitting surface thereof; and
wherein the edge is provided with a hinge joint, the curvature of the edge or of the light-emitting surface corresponding to the inner curvature of the inner sheath containing the optical means.

24. An endoscope according to claim 22, wherein the at least one diversion prism can be folded out by 90° and comprises a straight edge between the light entrance surface and a light-emitting surface thereof; and
wherein the edge is provided with at least one hinge joint, the edge being embedded in the inner sheath containing the optical means.

25. An endoscope comprising:
an essentially cylindrical shaft;
optical means, disposed in said shaft and having an optical axis which coincides with a longitudinal axis of the shaft, for passing optical images of an area to be observed from one end of the endoscope to another; and
optical fibers disposed in said shaft for illuminating the area to be observed, the optical fibers being arranged concentrically about the optical means and having a connecting piece disposed radially to the longitudinal axis of the shaft by which the optical fibers are connected to a fiber-optic cable which leads to an external light source;
wherein a viewing direction at an end of the endoscope nearer to the area to be observed is inclined to the longitudinal axis of the shaft;
wherein at least the end of the optical means nearer the area to be observed is arranged so as to rotate with respect to the connecting piece;
wherein a light-emitting surface of the illumination sheath is provided with a ring of flexible transparent material of a semi-circular cross-section which has a region which protrudes inwardly over the light-emitting surface; and wherein the inner sheath containing the optical means comprises a protrusion which deforms the protruding region of the ring by contact therewith so that illuminating light is diverted to correspond with a viewing direction and viewing angle of the optical means.

26. An endoscope comprising:

an essentially cylindrical shaft;

optical means, disposed in said shaft and having an optical axis which coincides with a longitudinal axis of the shaft, for passing optical images of an area to be observed from one end of the endoscope to another; and optical fibers disposed in said shaft for illuminating the area to be observed, the optical fibers being arranged concentrically about eh optical means and having a connecting piece disposed radially to the longitudinal axis of the shaft by which the optical fibers are connected to a fiber-optic cable which leads to an external light source;

wherein a viewing direction at an end of the endoscope nearer to the area to be observed is inclined to the longitudinal axis of the shaft;

wherein at least the end of the optical means nearer the area to be observed is arranged so as to rotate with respect to the connecting piece;

wherein a cover of non-deformable transparent material is provided which is rotatably mounted on a light-emitting surface of the illumination sheath, the material having a light-emitting surface inclined with respect to the light-emitting surface of the illumination sheath; and wherein the inner sheath containing the optical means can be fixed to the cover so that illuminating light is diverted to correspond with a viewing direction and viewing angle of the optical means.

* * * * *